(12) United States Patent
Lichtstein et al.

(10) Patent No.: US 7,087,590 B2
(45) Date of Patent: Aug. 8, 2006

(54) 19-NORBUFALIN DERIVATIVES, THEIR PREPARATION AND PHARMACEUTICAL COMPOSITIONS CONTAINING THEM

(75) Inventors: David Lichtstein, Jerusalem (IL); Joseph Deutsch, Jerusalem (IL)

(73) Assignee: Yissum Research Development Company of the Hebrew University of Jerusalem (IL)

( * ) Notice: Subject to any disclaimer, the term of this patent is extended or adjusted under 35 U.S.C. 154(b) by 253 days.

(21) Appl. No.: 10/257,884

(22) PCT Filed: Apr. 17, 2002

(86) PCT No.: PCT/IL01/00347

§ 371 (c)(1),
(2), (4) Date: Apr. 10, 2003

(87) PCT Pub. No.: WO01/79256

PCT Pub. Date: Oct. 25, 2001

(65) Prior Publication Data

US 2003/0162701 A1  Aug. 28, 2003

(30) Foreign Application Priority Data

Apr. 17, 2000 (IL) ...................... 135707

(51) Int. Cl.
*A61K 31/58* (2006.01)
*A61K 31/585* (2006.01)
*C07J 17/00* (2006.01)

(52) U.S. Cl. .......................... 514/172; 514/174; 540/94
(58) Field of Classification Search ................ 540/94; 514/172, 174
See application file for complete search history.

(56) References Cited

U.S. PATENT DOCUMENTS 5,874,423 A   2/1999   Lichtstein et al.

FOREIGN PATENT DOCUMENTS

WO   WO-94/05305 A1   3/1994

OTHER PUBLICATIONS

Bohl, et al., "Quantitative Structure-Activity Relationships Of Cardiotonic Steroids Using Empirical Molecular Electrostatic Potentials And Semiempirical Molecular Orbital Calculations", J. Steroid Biochem., vol. 21, No. 4, pp. 373-379, 1984.
Sen, et al., "A Simple And Efficient Synthesis of Bufalin", J. Chem. Commun., pp. 1213-1214, 1982.
Tsai, et al., "On Cardioactive Steriods.IX. The Conversion Of Digitoxigenin To Bufalin", Can. J. Chem., vol. 60, pp. 2161-2163, 1982.

Wiesner, et al., "On Cardioactive Steriods. XII. The Synthesis Of (Natural) Bufalin And x'-Isobufalin", Helvetica Chimica Acta, vol. 66, Fasc. 8, pp. 2632-2640, 1983.
Wiesner, et al., "On Cardioactive Steriods. VIII. The Synthesis Of Bufalin And Resibufogenin Isomers", Helvetica Chimica Acta, vol 65, Fasc 7, pp. 2049-2060, 1982.
Han, et al., "Neurosteroids Analogues. 4. The Effect Of Methyl Substitution At The C-5 and C-10 Positions of Neurosteroids On Electrophysiological Activity at GABAa", J. Med.Chem., vol. 39, pp. 4218-4232, 1996.
Tsai, et al., "A Simple Synthesis Of Cardenolides And Their Less Toxic Isomers Via Furyl Intermediates", Heterocycles, vol. 12, No. 11, pp. 1397-1402, 1979.
Lichtstein, et al., "Identification Of Digitalis-like Compounds in Human Cataractous Lenses", Eur. J. Biochem., vol. 216, pp. 261-268, 1993.
Sondheimer, et al., "Synthesis Of Bufadienotides. The Synthesis Of Bufalin And Resibufogenin", J. Am.Chem. Soc., vol. 91, No. 5, pp. 1228-1230, 1969.
Stache, et al., "Synthesen Von Bufadienoliden Synthese Von Scillarenin", Tetrahedron Letters, No. 35, pp. 3033-3038, 1969.
Pettit, et al., Synthesis Of buf-20(21)-enlides And bufa-20,22-dienolides, Can. J. of Chem., vol. 47, pp. 2511-2513, 1969.
Pettit, et al., "Bufadienolides. 1. Introduction and Base-Catalyzed Condensation of Methyl Ketones With Glyoxylic Acid", J. of Org. Chem., vol. 35, No. 5, pp. 1367-1376, 1970.
Almirante, et al., "Stereoselective Synthesis of New Digitalis-like Perhydroindene Derivatives From The Hajos-Parrish Ketone", Synlett, 22, pp. 1234-1236, 1998.

(Continued)

*Primary Examiner*—Barbara P. Badio
(74) *Attorney, Agent, or Firm*—Lerner, David, Littenberg, Krumholz & Mentlik, LLP

(57) ABSTRACT

A 19-norbufalin derivative compound of formula (I):

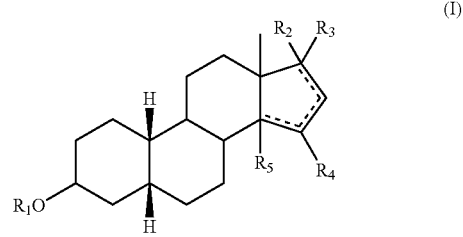

wherein the R groups are as defined by the present specification. The compounds are $Na^+K^-$-ATPase inhibitors and can be used in the treatment of cardiac and/or vascular malfunction, renal malfunction, as digoxin antagonists, for treatment of CNS disorders and for the treatment of malignant and proliferative cell diseases.

12 Claims, 7 Drawing Sheets

OTHER PUBLICATIONS

Wiesner, et al., "Some Resent Progress In The Synthetic And Medicinal Chemistry Of Cardioactive Steroid Glycosides", Pure & Appl. Chem., vol. 58, No. 5, pp. 799-810, 1986.

Di-Capua, et al., "Mass Spectral Determination Of the Configuration Of 17β-Tetrahydropranloxy-19-norandrostan-3β-ol", Int. J. Mass. Spectrom, 167/168, pp.

Han, et al., "An Improved Synthesis Of 18-Nor-ketosteroids And Application Of The Method For The Preparation Of (3b,5b,13b)-3-Hydroxygonan-17-one", J. Org. Chem., vol. 61. pp. 7614-7616, 1996.

Somay, et al., "Synthese de bromofurannes et de derives furanniques mono et disubstitues", Bull. Soc. Chem., No. 3, pp. 990-1000, 1971.

Chiarello, et al., "Synthetic Routes To Cristatic Acid And Derivatives", Tetruhedron, vol. 44, No. 1, pp. 41-48, 1988.

Kelly, et al., "Pharmacological Treatment Of Heart Failure", Goodman & Gilman's The Pharmacological Basis of Therapeutics, 8th ed., pp. 809-838, 1990.

Zhang, et al., "Induction by Bufalin Of Differentiation Of Human Leukemia Cells HL60, U937 and ML1 Toward Macrophage/Monocyte-like Cells And its Potent Synergistic Effect On The Differentiation Of Human Leukemia Cells In Combination with Other Inducers", Cancer research 52, pp. 4634-4641, 1992.

Numazawa, et al., "A Cardiotonic Steroid Bufalin-Induced Differentiation Of THP-1 Cells", Biochem. Pharma., vol. 52, pp. 321-329, 1996.

Watabe, et al., "The Cooperative Interaction Of Two Different Signaling Pathways In Response To Bufalin induces Apoptosis In Human Leukemia U937 Cells", J. Bio.Chem., vol. 271, Issue of Jun. 14, pp. 14067-14073, 1996.

9 mmHg 0.4 sec

19-NORBUFALIN DERIVATIVES, THEIR PREPARATION AND PHARMACEUTICAL COMPOSITIONS CONTAINING THEM

CROSS REFERENCE TO RELATED APPLICATION

The present application is the § 371 National Stage of International Application No. PCT/IL01/00347, filed Apr. 16, 2001, which claims the benefit under §119(a) of Israeli Application No. 135707, filed on Apr. 17, 2000.

FIELD OF THE INVENTION

The invention relates to novel 19-norbufalin derivatives and processes for their preparation. The novel norbufalin derivatives are inhibitors of $Na^+,K^+$-ATPase activity and can be used in the treatment of cardiovascular, kidney and malignant and proliferative cell diseases.

BACKGROUND OF THE INVENTION

Endogenous bufodienolides having digitalis-like activity were identified in material extracted and purified from human cataractous lenses by chemical ionization mass spectroscopy, together with UV spectroscopy and biological characterization, as 19-norbufalin and 19-norbufalin peptide conjugate [Lichtstein D., et al., Eur. J. Biochem. 216: 261–268 (1993); U.S. Pat. No. 5,874,423].

Since 1969 several attempts to synthesize bufodienolides were reported [Soncheimer F., et al., J. Am. Chem. Soc. 91:1228–1230 (1969); Stache U., et al., Tetrahedron Lett., 35:3033–3038 (1969); Pettit G. R., et al., Can. J. Chem., 47:2511 (1969); Pettit G. R., et al., J. Org. Chem., 35:1367–9 (1970)]. In all reports the starting material was a steroid compound in which the functional groups were altered in order to produce the active bufadienolide molecule. The transformation of digoxin to a bufodienolide compound was also reported [Pettit G. R., et al., ibid.]. In the early 1970, it was already established that for a biologically active cardiolide the C/D cis ring junction, the 17β-butenolide moiety and the 3β,14β-dihydroxy are the main prerequisites. The A/B ring junction can be cis and trans without a dramatic change of activity [N. Almirante, et al., Synthetic Letters, 22:1234–1236 (1998)].

The most advanced synthesis of bufalin and its analogs was reported ten years later [Tsay T. Y. R., et al., Heterocycles, 12:1397–1402 (1979); Sen A., et al., J. Chem. Soc. Chem. Comm. 66:1213–1214 (1982); Wiesner K., et al., Helv. Chim. Acta, 66:2632–2641 (1983); Weisner K. A. & Tsai T. I. R., Pure and Appl. Chem., 53:799–810 (1986)]. According to these reports, a 3β-benzyloxy-α,β-unsaturated-17-keto steroid, was reacted with a lithiated ethyleneacetal of 2-furaldehyde and the product was further transformed in the bufodienolide compound in a multistep process.

In search for synthetic compounds with digitalis-like activity, the present inventors have developed a novel process for the synthesis of 3α and 3β-isomers and analogs of 19-norbufalin, which is the subject of the present invention.

The $Na^+,K^+$-ATPase (E.C.3.6.1.3) is an integral plasma membrane protein which is responsible for maintaining sodium and potassium ions gradient in all eukaryotic cells. This enzyme has a high-affinity receptor for digitalis steroids and endogenous ligands for these receptors have been postulated, which regulate the $Na^+,K^+$-pump activity. Indeed, digitalis-like compounds have been shown to be present in diverse mammalian and amphibian tissues.

Naturally occurring and synthetic digitalis-like compounds may be used as therapeutic agent in the treatment of various pathological conditions in which involvement of endogenous digitalis-like compounds is implied. Such compounds may be used as cardiotonic agents, increasing the intensity of heart muscle contractions, as vasoactive agents, elevating blood pressure. and as natriuretic/diuretic agents, increasing the excretion of sodium into the urine and thus increasing urine volume. In view of the marked involvement of $Na^+,K^+$-ATPase in the central nervous system, digitalis like compounds may also be used as neuromodulating agents. Cardiac glycosides, such as ouabain and bufalin, have been reported to induce cell differentiation and cell apoptosis. The synthetic compounds of the invention can also be used for the treatment of various proliferative cell anid malignant diseases.

SUMMARY OF THE INVENTION

The present invention relates to compounds of formula (I)

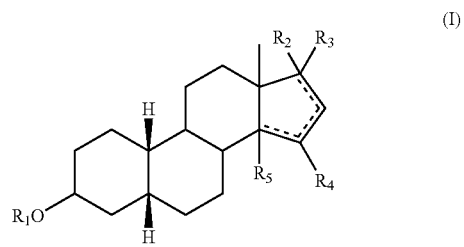

(I)

wherein
$R_1$ is hydrogen or a hydroxy protecting group, wherein said hydroxy protecting group is preferably selected from benzyl (hereinafter "Bz"), amino acid, peptide and mono- and di-saccharide;

$R_2$ is OH or hydrogen;

$R_3$ is selected from one of the following groups:

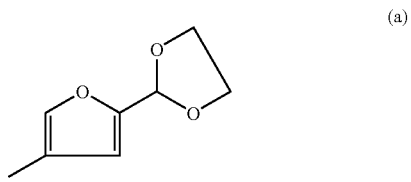

(a)

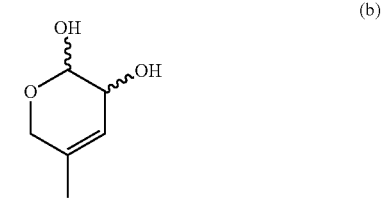

(b)

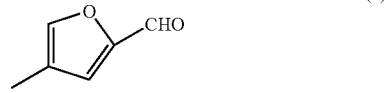

(c)

-continued

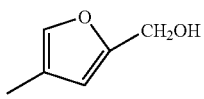
(d)

$R_4$ is hydrogen or OH;
$R_5$ is hydrogen or OH; and
the dashed he in formula (I) denotes an optional double bond;

and isomers and pharmaceutically acceptable salts thereof.

Particular compounds according to the invention are the compounds designated herein as compounds 13, 13-1, 13-2, 13-3, 14 and 17.

The invention also relates to a process for the preparation of compounds of formula (I) and its intermediates. The process of the invention may also be used for the preparation of compounds of formula (1) wherein $R_5$ is the group

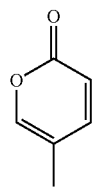
(e)

particularly for the preparation of the compounds designated herein as compounds 18, 19 and 20.

Further, the invention relates to pharmaceutical compositions comprising as active ingredient a compound of formula (I), wherein the substituents are as defined above, or pharmaceutical acceptable salts thereof, in a pharmaceutically acceptable carrier, optionally further comprising pharmaceutically acceptable adjuvants, excipients or diluents.

The invention further relates to methods of treating and/or preventing cardiac, vascular and/or renal malfunction in patients in need of such treatment comprising administering to said patient a therapeutically effective amount of a compound of formula (I), wherein the substitutes are as defined above, or of a pharmaceutical composition according to the invention. The invention also relates to methods of treating digoxin intoxication by administering to a patient in need of such treatment a therapeutically effective amount of a compound of formula (I), wherein the substitutes are as defined above, or of a composition according to the invention. The invention also provides methods for treating a central nervous system disorder in a patient in need of such treatment comprising administering to said patient a therapeutically effective amount of a compound of formula (I), wherein the substitutes are as defined above, or of a composition according to the invention.

Further, the invention provides methods of treating a malignant disease in a patient in need of such treatment comprising administering to said patient a therapeutically effective amount of a compound of formula (I), wherein the substituents are as defined above, or a composition according to the invention.

The invention also relates to use of a compound of formula (I), wherein the substituents are as defined above, in the preparation of pharmaceutical composition.

DETAILED DESCRIPTION OF THE INVENTION

The present invention relates to compounds of the general formula (I):

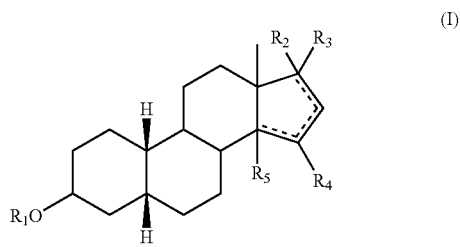
(I)

wherein $R_1$ is hydrogen or a hydroxy protecting group, wherein said hydroxy protecting group is preferably selected from benzyl (hereinafter "Bz"), amino acid, peptide and mono- or disaccharide;

$R_2$ is OH or hydrogen;

$R_3$ is selected from one of the following groups:

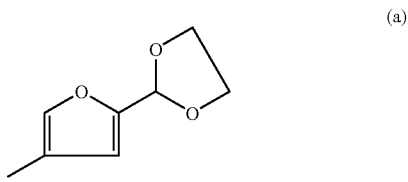
(a)

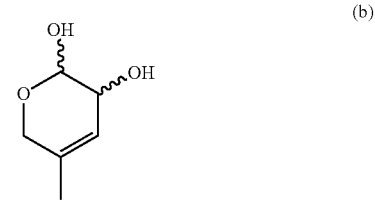
(b)

(c)

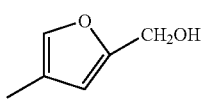

(d)

R₄ is hydrogen or OH;

R₅ is hydrogen or OH;

and the dashed line in formula (I) denotes an optional double bond;

and isomers pharmaceutically acceptable salts thereof.

The hydroxy protecting group may be any suitable such group, as known to the man of skill in the art of chemical synthesis. Preferred hydroxy protecting groups are benzyl, amino acids, peptides, preferably of from 2 to 20 amino acid residues, mono- and di-saccharides.

Figure 2:
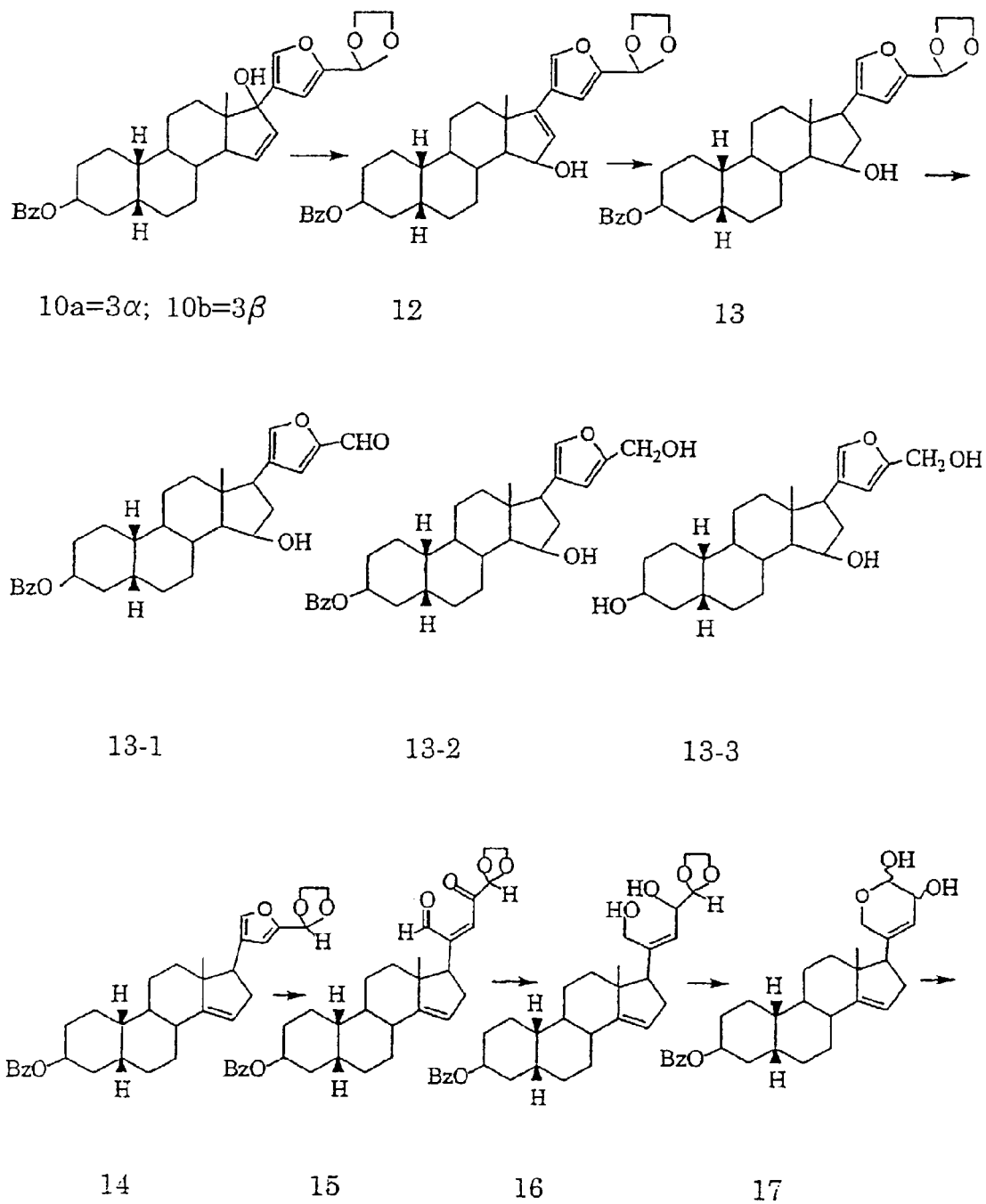
FIGS. 2 and 2a Schematic representation of the preparation of compounds 10 to 20, and their structural formulae.
Figure 2A:
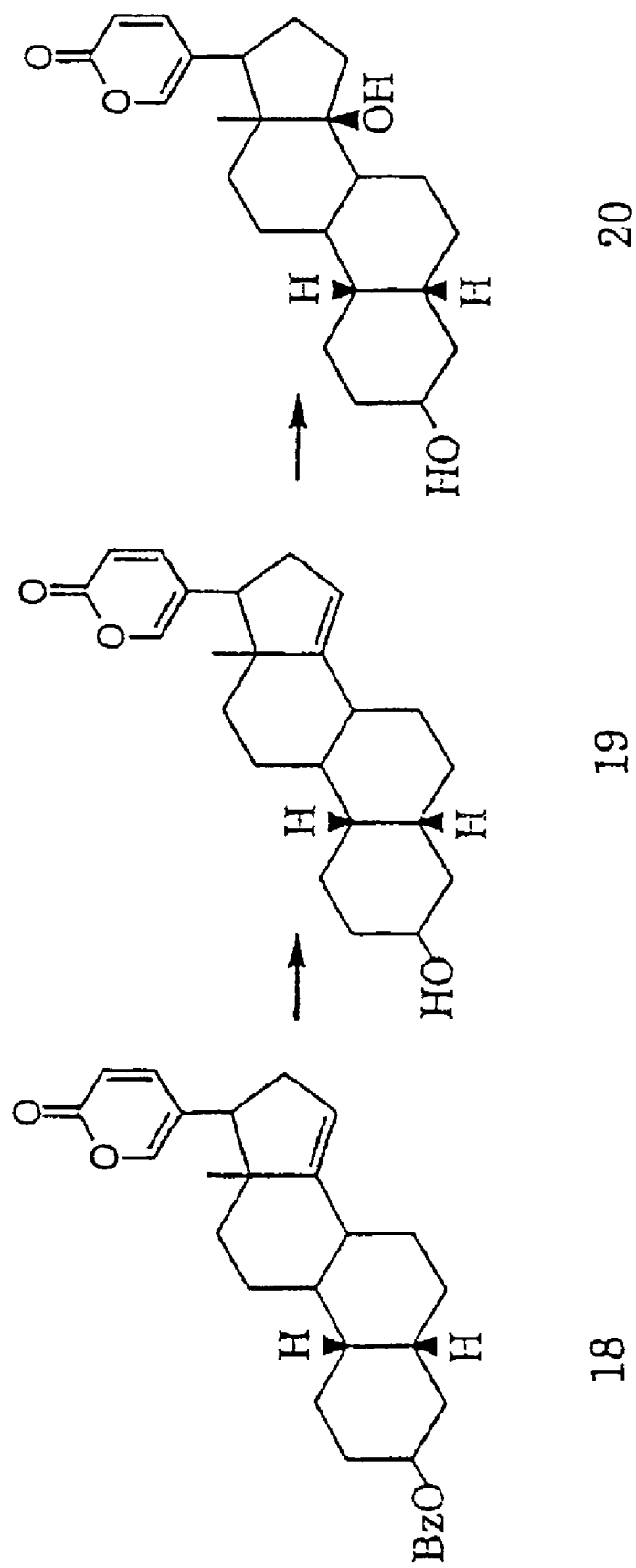

The invention particularly relates to a compound of formula (I) in which $R_1$ is Bz, $R_2$ is OH, $R_3$ is the group (a) and $R_4$ and $R_5$ are hydrogen, having a double bond between the carbons at the 15 and 16 positions, herein designated compound 10 (FIG. 2).

The invention further relates to a compound of formula (I) in which $R_1$ is Bz, $R_2$ is hydrogen, $R_3$ is the group (a), $R_4$ is OH and $R_5$ is hydrogen, herein designated compound 13 (FIG. 2).

Further, the invention particularly relates to a compound of formula (I) in which $R_1$ is Bz, $R_2$ is hydrogen, $R_3$ is the group (c), $R_4$ is OH and $R_5$ is hydrogen, herein designated compound 13-1, a compound of formula (I) in which $R_1$ is Bz, $R_2$ is hydrogen, $R_3$ is the group (d), $R_4$ is OH and $R_5$ is hydrogen, herein designated compound 13-2 and a compound of formula (I) in which $R_1$ is hydrogen, $R_2$ is hydrogen, $R_3$ is the group (c), $R_4$ is OH and $R_5$ is hydrogen, herein designated compound 13-3 (FIG. 2).

Another particular compound is a compound of formula (I) in which $R_1$ is Bz, $R_2$ is hydrogen, $R_3$ is the group (a) and $R_4$ is hydrogen, having a double bond between the carbon atoms at the 14 and 15 positions, herein designated compound 14 (FIG. 2).

Further the invention relates to a compound of formula (I) in which $R_1$ is Bz, $R_2$ is hydrogen, $R_3$ is the group (b) and $R_4$ is hydrogen, having a double bond between the carbon atoms at the 14 and 15 positions, herein designated compound 17 (FIG. 2).

The novel compounds of the invention are very similar in structure to the known digitalis and bufodienolides. As will be shown in the Examples, these synthetic isomers of norbufalin have, like the known cardienolides, effects on cardiac and smooth muscle contractility and kidney and neuronal function and can be used as drugs affecting the cardiovascular and other systems involving the $Na^+,K^+$-ATPase. An important finding is that the compounds of the invention are considerably less toxic that the abundantly used digoxin. Moreover, the compounds of the invention may antagonize digoxin, and thus can serve for treating digoxin intoxication.

Figure 1:
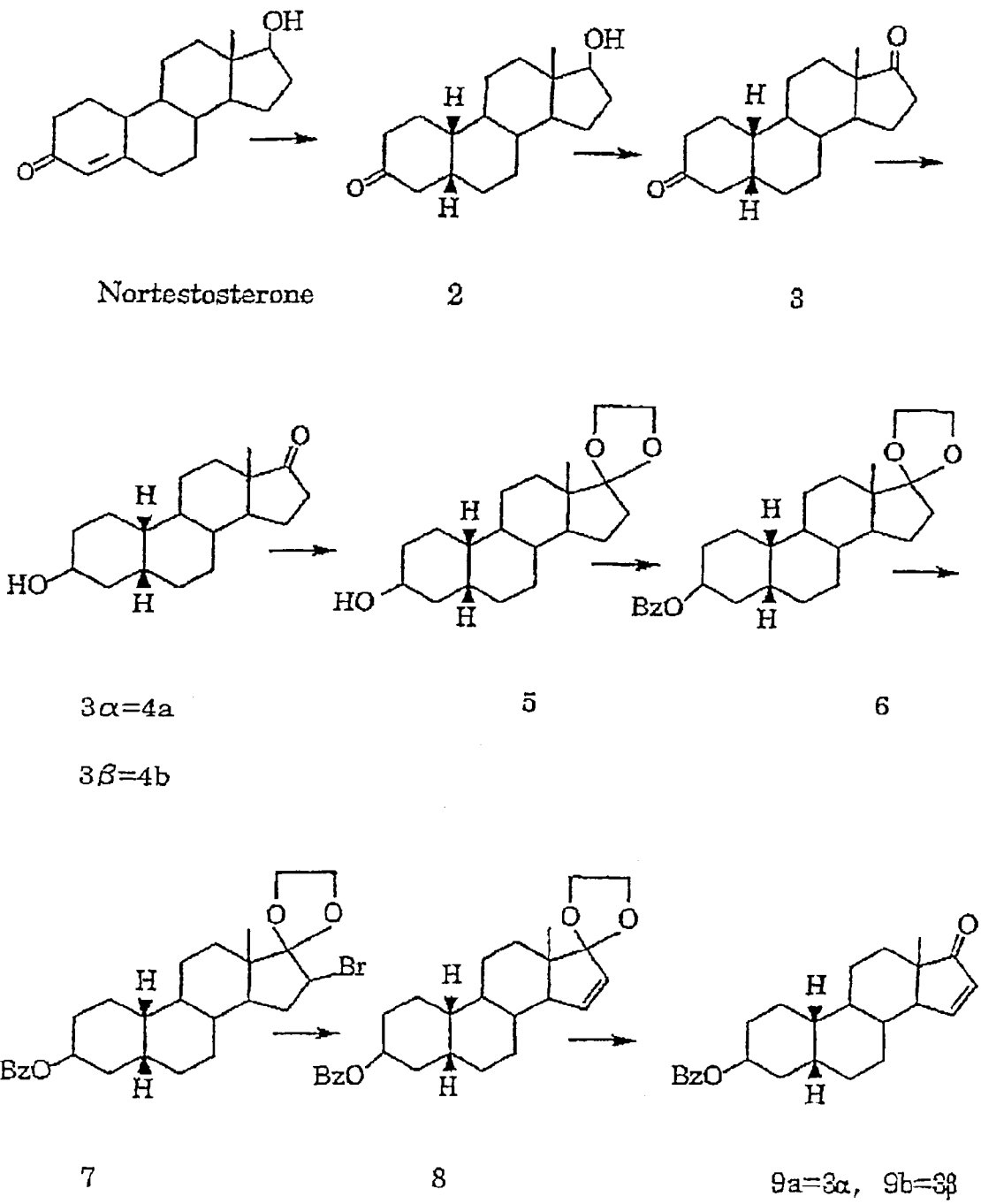
FIG. 1 Schematic representation of the preparation of compounds 1 to 9, and their structural formulae.

The synthesis of bufalin contains three major steps. The first step is the synthesis of 3α- and 3β-benzyloxy-5-estr-15-en-17-one. These compounds are illustrated in FIG. 1, as compounds 9a and 9b . The second step is the reaction of the estrane (norandrostane) moiety with the 4-bromofurfural ethylene acetal, followed by the third step, which is the transformation of the furfural moiety into pyrone.

The invention also relates to a process for the preparation of compounds of formula (I), as well as their various intermediates, schematically illustrated in FIGS. 1 and 2. The process of the invention generally involves the following steps:

First, the double bond of 19-nortestosterone (FIG. 1) is hydrogenated, to give compound 2. The hydroxyl group of compound 2 is then oxidized, to give compound 3, followed by reduction of the carbonyl group at position 3 of compound 3, to a hydroxyl group, to give compound 4. Isomerization occurs at position 3, yielding the two isomers, α and β.

The following steps can be performed with either of the two isomers. Compound 4 is reacted with ethylene glycol to give its ketal derivative, compound 5. Then, the hydroxyl group of compound 5 is protected by a benzyl protecting group, to give compound 6. Compound 6 is first brominated at position 16, and the product 7, is then debrominated, to give compound 8. Hydrolysis of the ketal group of compound 8 produced compound 9, a mixture of 3 alpha and 3 beta isomers at a ratio of 4:6 respectively, which were separated by chromatography on silica gel. Compound 9 was further reacted with bromo-furfural ethylene acetal, to give compound 10 (FIG. 2).

The purified 10, was first acetylated to compound 11 (not shown in FIG. 2) and subjected to allylic rearrangement in aqueous acetone in presence of $CaCO_3$ to give the allylic alcohol 12. The plied product was hydrogenated on $Pd/CaCO_3$ in methanol to give a crystalline alcohol 13. The X-ray diffraction pattern of compound 13, supported the assumed structures. Before proceeding to the synthesis of compound 14, compound 13 was hydrolyzed to aldehyde13-1, and reduced with $NaBH_4$ to the diol 13-2. Deprotection of the hydroxy soup at position 3, by hydrogenolysis on $Pd(O)_2$ give the triol (13-3).

In order to transform the furyl ring into the pyrone ring, first the compound 13 was dehydrated to give compound 14. After purification compound 14 was oxidized with NBS to the keto aldehyde 15, which without isolation was immediately reduced with $NaBH_4$ at room temperature to diol 16. Compound 16 was subjected to hydrolysis and cyclization without additional purification to give the hemiacetal 17.

The intermediates so produced may be for preparing compounds of formula (I) in which R3 represents the group

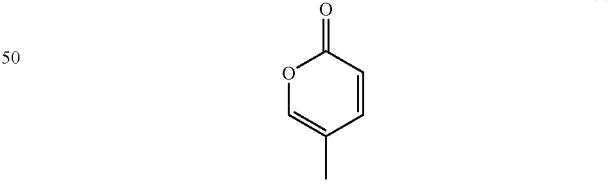

(e)

Thus, treatment with pyridinium chloroperchromate oxidized and dehydrated the hemiacetal 17 to give the pyrone 18, which, in turn is hydrogenolyzed to remove the benzyl protecting group from position 3, to give compound 19. Compound 19 was hydroxylated at the 14 position by a peroxidation technique to give either (5α- or 3β-norbufalin, depending on the isomer of compound 9 that was used.

As will be shown in the following Examples, at the first step, the synthesis of 3αOH and 3βOH androstane moieties was implemented by a modification of published procedures [Tsay T. Y. R., et al., ibid.]. The synthesis uses as starting material compound 19-nortestosterone (FIG. 1) which by hydrogenation on $RhCl_3$ hydrate produced a saturated hydroxyketone (compound 2) with the A/B ring junction being cis [Di-Capua, S., et al., Int. J. Mass Spectrom. 167/16S:79–85 (1997)]. Oxidation with $CrO_3$ at 4° C. converted the hydroxyketone (compound 2) to a diketone (compound 3) [Han, M. & Convey D. F., J. Org. Chem. 61:7614–7616 (1996)]. Stereo- and site-selective reduction of the 3-keto group with K Selectride [Han M., Zorumski, C. F., and Convey. D. F., J. Med. Chem. 39: 4218–4220 (1996)] yielded in a mixture of 3α- and 3β-hydroxy5β-estran-17-one steroids (compound 4). The ratios of the two isomers depend on the scale of the synthesis (up to 2 g, sythesis of only 3βOH was obtained). Before benzyloxylation, the ketone at the 17 position (compound 4) was protacted as ethylene ketal and then submitted to benzyloxylation in presence of NaH in toluene. Selective bromination followed by dehydrobromination and deprotection by cleavage of the ketal group yielded the α,β unsaturated ketone (compound 9) in an overall yield of 15%. The 3α- and 3β-benzyloxy-5β-estr-15-en-17-one were obtained at a ratio of 4:6, respectively, and were separated by flash chromatography on silica gel.

Further, compound 9 was condensed with 4Br-furaldehyde ethyleneacetal [Sorney R., et al., Bull. Chem. Soc. France 3:990–1000 (1971); Chiarello J. & Joullie M., Terahedron 44:41–48 (1988)] to give compound 10 (FIG. 2). The purifed tertiary alcohol was acetylated with acetic anhydride in pyridine to compound 11, which without purification was subjected to allylic rearrangement in boiling aqueous acetone and $CaCO_3$ to yield the allylic alcohol (compound 12). The purified product was hydrogenated on $Pd/CaCO_3$ in methanol and traces of NaOAc solution, yielding the hydroxy at position 15 crystalline product (compound 13). The X ray diffraction pattern of the crystalline 3α,15-dihydroxy17-furyl steroid confirmed the stereochemistry of the 3α-hydroxy, 15β-hydroxy and 17β-furyl groups in the steroid.

Compound 13 may serve as a starting material for the preparation of compound 14 and also of compounds 13-1, 13-2 and 13-3.

Before proceeding with the synthesis of compound 14, compound 13 was hydrolyzed to aldehyde 13-1, and reduced with $NaBH_4$ to the diol 13-2. Deprotection of the 3-hydroxy group by hydrogenolysis on $Pd(OH)_2$ gave the triol (13-3).

In order to prepare compound 14, the crystalline product (compound 13) was dehydrated by treatment with thionylchloride in pyridine to give compound 14. Further, compound 14 was dissolved in dioxane/water and treated with NBS at room temperature. After addition of NBS, the keto aldehyde (compound 15) was reduced with $NaBH_4$ diol 16. Compound 16 was subjected to cyclization without any purification in boiling THF in presence of HCl. In this process, hydrolysis of the ethylene acetal is followed by a cyclization process to give the hemiacetal product (compound 17).

In order to prepare compounds 18, 19 and 20, which are also biologically active, compound 17 was subjected to a mild oxidation with pyridinium chloroperchromate. In addition to the oxidation of the hemiacetal hydroxyl group, a dehydration of the second hydroxyl and rearrangement of the double bond take place, yielding into the pyrone (compound 18). Next, the benzyl group from the 3OH position was removed by hydrogenolysis on $Pd(OH)_2$ to give compound 19. The 14OH group is inserted by a peroxidation technique, treating compound 19 with NBS in presence of a catalytic amount of $HClO_4$, followed by hydrogenolysis of the Br atom with active Raney-Ni to give compound 20.

The inventors have interestingly found that compounds of formula (I), and some of their intermediates, and particularly compounds 13, 13-1, 13-2, 13-3 and 14 to 17 (FIG. 2) are inhibitors of $Na^+,K^+$-ATPase activity. As shown in Table 1, the compounds inhibit the activity of the $Na^+,K^+$-ATPase in a dose-dependent manner, without significantly affecting the activity of the $Mg^{++}$-ATPase. Thus, since the $Na^+,K^+$-ATPase is involved in numerous functions of the living cells, the novel compounds of the invention will possess all known pharmacological effects attributed to sodium pump inhibitors [Hoffmann, B. F. & Bigger, J. T., Jr., Digitalis and allied cardiac glycosides, In: The Pharmacological Basis of Therapeutics (Goodman Gilman, A., et al., eds.), 8th Edition, Pergamon Press, New York, pp. 814–839 (1990)].

Figure 3A:
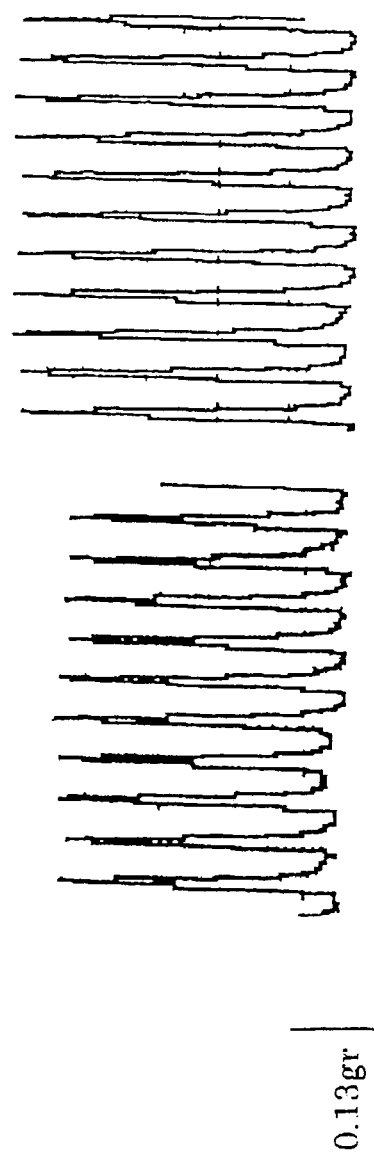
FIGS. 3a and 3b Effect of compounds of the invention on guinea pig atrial muscle contractilty.

For example, the main pharmacological effect of digitalis is increasing the force of contraction of heart muscle. Indeed as can be seen in FIG. 3a, the addition of the compound 13b (the β isomer of compound 13, see FIG. 2) to guinea pig atrial muscle preparation, induced about 30% increase in the force of contraction after 10 minutes. In vivo experiments (data not shown herein) demonstrated that compound 13b was not toxic when injected to guinea pigs at doses of up to 13 mg/kg, while injection of digoxin at such doses is lethal.

Thus, considering the inhibitory activity on $Na^+,K^+$-ATPase by the compounds of the invention, they may be used in the treatment and prevention of cardiac and renal malfunctions involving $Na^+,K^+$-ATPase, such as arrhythmia and cardiac failure, induction of natriuresis and diuresis, and constriction of smooth muscle in arterioles, causing elevation of blood pressure. In addition, the compounds of the invention call be used as neuromodulators, affecting the central nervous system.

Digoxin is widely used as an inotropic drug to treat heart failure. Drugs to treat congestive heart failure accounted about $1.1 billion in the U.S. in 1999, while digoxin captures a significant segment of this market. High levels of digoxin in the plasma trigger heart arrhythmia and death (i.e. digitalis intoxication). Many physicians declare that every patient treated with digoxin may one day suffer a digoxin intoxication. The narrow "therapeutic index" of digoxin, i.e., interval between relief and intoxication, forces fine tuning of the dose, specific for every patient, and changed often. The novel compounds of the invention, as exemplified herein, may be efficiently replace digoxin in the treatment of heart failure and cardiovascular diseases by regulating the sodium/potassium pump and hence, intracellular sodium/potassium levels. As will be shown in the in vivo experiments herein, the novel compounds of the invention are not toxic for up to 13 mg/kg in guinea pigs, while an identical, and even much lower digoxin dose, is lethal.

Natural digitalis-like cardiolides have the β configuration. Without being bound to any theory, the β-isomers of the synthetic compounds of the present invention have also been shown to possess cardiolide activity.

Surprisingly, the inventors have shown that the α isomers of the compounds of the invention, although devoid of cardiolide activity, may act as digoxin antagonists, and could thus be used for treating digoxin intoxication. Therefore, the invention also relates to the use of the compounds of formula (I), particularly the α isomers in the treatment of digoxin intoxication and so pharmaceutical compositions for treating digoxin intoxication comprising compounds of formula (I), particularly the α isomers.

The most frequently used anti-cancer drugs are divided into several groups. These include compounds that act as anti purine-pyrimidine intermediates (such as methotrexate, 5'-fluorouracyl), compounds that bind to DNA (such as nitrogen mustards, cyclophosphamide, cisplatin, Doxorubicin), chromatin function inhibitors that inhibit cell division (topoisomerase inhibitors like etoposide, microtubules inhibitors such as vincristine, vinblastine and taxol), and endocrine function modifiers (prednisone, tamoxifen and testosterone) [see Pharmacological basis of Therapeutics (Goodman Gilman A., Rall T. W., Nies A. S., Taylor P., eds.) 8th edition, Pergamon Press, New York, 814–839 (1990)]. None of these compounds is aimed at the differentiation step in cell cycle. Recently, evidence has been presented that cardiac glycosides such as ouabain and bufalin induce cell differentiation and cell apoptosis [Zhang, L., et al., Cancer Res. 53:943–949 (1993); Numazawa, S. et al., Biochem. Pharmacol 52:321–329 (1996); Watabe, M. et al., J. Biol. Chem. 271:14067–14072 (1996).

As will be shown in the following Examples, and particularly Example 4 and FIGS. 4a to 4f, the compounds of the present invention are capable of inducing cell differentiation and apoptosis and thus work in a pathway that is completely different from those of the above anti-cancer drugs. The use of these compounds may not only substitute the current drugs, but may be a complementary treatment for the various malignancies.

Thus, the compounds of the invention can also be used as modulators of cell differentiation and as inducers of cell apoptosis, alone, or in combination with other anti-cancer drugs.

In this aspect, the invention relates to pharmaceutical compositions comprising as active ingredient at least one compound of compound of formula I. Preferably, the active agents are compounds herein designated 13 to 20 (FIGS. 1 and 2).

The pharmaceutical compositions of the invention are preferably intended for the treatment and/or prevention of malfunctions involving the $Na^+,K^+$-ATPase. The pharmaceutical compositions of the invention may be used in the treatment and/or prevention of cardiac and renal malfunctions involving $Na^+,K^+$-ATPase, such as arrhythmia and cardiac failure, for induction of natriuresis and diuresis, and for constriction of smooth muscle in arterioles, causing elevation of blood pressure. In addition, the pharmaceutical compositions of the invention can be used as neuromodulators, affecting the central nervous system.

Further, the pharmaceutical compositions of the invention can be used for modulating cell differentiation and cell apoptosis, and in the treatment of malignant and proliferative cell diseases. These composition may contain as active ingredient at least one compound of Formula I, and optionally contain an additional, anti-cancer drug.

The pharmaceutical compositions of the invention may contain, in addition to the active agent, conventional non-toxic, pharmaceutically acceptable carriers, diluents, adjuvants and vehicles. As used herein, the term "pharmaceutically acceptable carrier, diluent, adjuvant and vehicle" means an inert non-toxic solid or liquid filler, diluent or encapsulating material, not reacting with the active ingredient. These carriers are known to those skilled in the art of pharmacology. Wetting agents, emulsifers and lubricants, as well as coloring agents, release agents, coating agents, flavouring agents and preservatives can also be present in the compositions of the invention.

The compositions of the invention may be administered orally or parenterally. The term parenterally as used herein includes subcutaneous, intravenous, intramuscular, intraarticular and intratechal injection or infusion, sub-cutaneous implants or targeted delivery systems, such as monoclonal antibodies, vectored delivery, iontotrophic, polymeric matrices, liposomes and microspheres.

The compositions may be in dosage unit form, that may contain daily required amounts of the compounds of the invention or submultiples thereof to make up the desired dose. The specific therapeutically effective does level for any particular patient will depend upon a variety of factors, including the activity of the specific compound used, the age, body weight, general health, sex, diet, time of administration, route of administration, rate of excretion, etc., and will be determined by the attending physician. The treatment generally has a length proportional to the length of the disease and the drug effectiveness.

The invention also provides methods of preventing or treating cardiac and renal malfunctions involving $Na^+,K^+$-ATPase, such as arrhythmia and cardiac failure, methods of inducing natriuresis and diuresis, and of constricting smooth muscle in arterioles, causing elevation of blood pressure. In addition, the invention provides for methods of modulating activity of the central nervous system. Further, the invention provides a method for the treatment of proliferative cell diseases, where modulation of cell differentiation and cell apoptosis is required. The methods treatment of the invention comprise administering to a patient in need of such treatment a therapeutically effective amount of at least one compound of formula I, or of a pharmaceutical composition containing the same. Administration may be in any of the routes describes above.

EXAMPLES

Materials and Methods

Solvents were purchased from Biolab (Jerusalem, Israel), Aldrich Chemical (Milwaukee, Ill.) and Frutarom (Haifa, Israel). Chemical reagents and, in particular, 19-nortestosterone (compound 1), $RhCl_3.H_2O$, Aliquat-336®, n-butyllithium, K-Selectride®, pyridinium tribromide, potassium-t-butoxide and NBS were purchased from Aldrich Chemical Co, (Milwaukee, Ill.). 3- and 4-Bromo-2-furaldehyde was synthesized according to Sorney R., et al., Bull. Chem. Soc. France 3:990–1000 (1971); Chiarello J. & Joullie M., Terahedron 44:41–48 (1988).

Electron Impact mass spectra was obtained with either an LKB 2091 (Broma, Sweden) or Thermo-Quest Trace MS (San Jose, Calif.) mass spectrometer operating at 70 eV and with the ion source heated at 200° C. The samples were inserted by direct inlet with external heating up to 220° C. The 1H NMR(300 MHz) measurements were performed with a Varian VXR-300S (Palo Alto, Calif.) spectrometer in $CDCl_3$.

IR spectra were recorded on a Perkin Elmer FT-2000 or an Analect FT-IR spectrometer (Analect Instruments FX-6160, Irvine, Calif.). Liquid samples were recorded a film between two NaCl plates. Solid samples were pressed into KBr pellets.

Melting points were observed on an electrothermal apparatus (Electrothermal, England) and are uncorrected. Elemental analysis were performed by Microanalytical Laboratory at the Hebrew University, Givat Ram, Jerusalem, Israel.

The synthetic procedures of 3α (a) and 3β (b) isomers are identical, thus a general procedure is described. The spectral characterization of each isomer is included.

Synthetic Examples

17β-hydroxy-5β-estran-3-one (Compound 2)

A solution of 19-nortestosterone (10.0 g, 35.5 mmol) in dichloromethane (100.0 ml) was mixed with the catalyst previously prepared from $RhCl_3.H_2O$ (380 mg) and Aliquat-336® (800 mg) in water (10.0 ml) and dichloromethane (22.0 ml). The mixture was hydrogenated overnight at 20 psi. The product was washed twice with water (40 ml) and dried on $Na_2SO_4$. The catalyst was removed by flash-chromatography on silica gel with $CH_2Cl_2$ as eluant to give 10.5 g (92% yield) the title compound as a white solid.

MS: m/z ($M^+$) 276.

5β-estrane-3,17-dione (Compound 3)

To a stirred mixture of $CrO_3$ (15.0 g) in pyridine (100 ml), a solution of compound 2 (12 g, 43.4 mmol) in pyridine (60 ml) was added slowly at 0° C. The mixture was stirred overnight at 4° C. The reaction was stopped by the addition of water (200 ml). The product was extracted with ethyl acetate, washed with 5% HCl, brine and dried on $Na_2SO_4$. Evaporation of the solvent yielded a solid, which was submitted to reduction with K-Selectride without further purification. Crystallization from ethyl acetate produced a white solid, m.p. 182–184° C.

TLC: Eluant: EtOAc:Hexane (6:4), $R_f$ 0.70 MS: m/z ($M^+$) 274. IR 1737, 1705 $cm^{-1}$. $^1H$ NMR: δ=2.58(t, 1H, J=16 Hz, 4-$H_{ax}$), 0.88 (s, 3H, $CH_3$[1S]). Elemental Analysis: Calc. C, (78.8%); H, (9.48%). Found: C, (78.64%); H, (9.21%).

3-hydroxy-5βestran-17-one (Compound 4)

K-Selectride (11.8 ml, 11.8 mmol, 1.0 M solution in THF) was added, under nitrogen, to a solution of compound 3 (2.14 g, 7.8 mmol) in freshly distilled dry THF (200 ml) at −70° C. After 7 hr the reaction was stopped by addition of 10% NaOH (30 ml) and 30% $H_2O_2$ (30 ml). The reaction mxture was allowed to warm up to room temperature and the stirring continued for 30 additional minutes. The mixture was extracted with EtOAc, washed with brine (5×100 ml) and dried on $Na_2SO_4$. Removal of the solvents under reduced pressure give 2 g (92.9% yield) of the title compound as white solid powder.

4a: TLC: Eluant: EtOAc:Hexane (6:4), $R_f$ 0.65 MS: m/z ($M^+$) 276. IR 3472, 1725 $cm^{-1}$. $^1H$ NMR: δ=4.15 (m, 1H, 3-CHOH), 0.85 (s, 3H, $CH_3$).

When the previous procedure was scaled up to 10 g of compound 3, a mixture of the 4a and 4b isomers was obtained (31%, 61%, respectively). Separation of the isomers is described hereunder (proceduze 9). 4b: MS: m/z ($M^+$) 276. IR 3472, 1717 $cm^{-1}$. $^1H$ NMR: δ=3.7(m, 1H, 3-CHOH), 0.85(s, 3H, $CH_3$[18]).

3-hydroxy-5β-estran-17-one ethylene ketal (Compound 5)

Compound 4(10 g, 36.2 mmol) was dissolved in dry benzene (150 ml) mixed with ethylene glycol (25 ml, 280 mmol) and pyridinium p-toluenesulfonate (1 g, 3.9 mmol) and refluxed using a Dean-stark separator overnight till no starting material was detected by TLC. The cold solution was diluted with EtOAc (100 ml), washed twice with brine, dried on $Na_2SO_4$ and the solvents removed under reduced pressure. Flash-chromatography on silica gel with EtOAc:Hexane 4:6 as eluant to give 11.0 g (94.5% yield) the title compound as a white solid.

TLC: Eluant: Diethyl ether:Hexane(1:1), $R_f$ 0.30. MS: m/z ($M^+$) 320. IR 3343, 1788 $cm^{-1}$. $^1$NMR: δ=4.11(m, 1H, CHOH), 3.81(m, 4H,$OCH_2CH_2O$), 0.87(s, 3H, $CH_3$[18]).

3-Benzyloxy-5β-estran-17one-ethylene ketal (Compound 6)

A solution of compound 5 (6.0 g, 18.7 mmol) in dry toluene (80 ml) was refluxed in a system fitted with a Dean Stark separator. After 30 min, NaH powder (1.5 g, 60 mmol) was added and the reflux was continued for additional 30 min. Benzyl bromide (3.2 g, 18.7 mmol) was added slowly through a syringe under nitrogen and the mixture refluxed for 2 additional hours. After cooling, the toluene solution was poured slowly in ice. The organic phase was separated, washed with water and the toluene evaporated under reduced pressure. The oily product was dissolved in $CH_2Cl_2$, washed with water and dried on $Na_2SO_4$. Removal of the solvent produced an oily product. The oily product was dissolved in hexane, filtered and the hexane removed under reduced pressure. Flash-chromatography on silica gel with diethyl ether:hexane (1:9) as eluant give 6.2 g (80.8% yield) the title compound as a white solid.

6a: TLC: Eluant-Diethyl ether:Hexane (1:1), $R_f$ 0.55. MS: m/z ($M^+$) 410. $^1H$ NMR: δ=7.35(m, 5H, Ph), 4.50 (s, 2H, $CH_2$Ph), 3.89(m, 4H, $OCH_2CH_2O$), 3.38(m, 1H, H—C(3)), 0.83(s, 3H, $CH_3$[18]). 6b: TLC: Eluant: Diethyl ether:Hexane(1:1), $R_f$ 0.60. MS: m/z ($M^+$) 410. $^1H$ NMR: δ=7.35 (m, 5H, Ph), 4.14(s, 2H, $CH_2$Ph), 3.89(m, 4H, $OCH_2CH_2O$), 3.66(m, H—C(3). 0.85(s, 3H, $CH_3$[18]).

3benzyloxy-16-bromo-5β-estran-17-one ethylene ketal (Compound 7)

To a stirred solution of compound 6 (2.71 g, 6.6 mmol) in dry THF (15 ml), pyridinium tribromide (3 g, 8.4 mmol) was added slowly. After 20 h at 4° C. the mixture was poured into a cold solution prepared from 5% $NaHCO_3$ (10 ml) and 10% $Na_2S_2O_3$ (10 ml). The organic phase was extracted with diethyl ether (2×100 ml) washed with brine, dried on $Na_2SO_4$ and the solvent removed under reduced pressue. The product was dissolved in hexane, filtered and the solvent removed to give 3 g (93.1% yield) the title compound as an oil. The crude oil was subjected to dehydrobromination without additional purification.

TLC: Eluant: Diethyl ether:hexane (1:1), $R_f$ 0.80. MS: m/z ($M^+$) 488, 490, [M-Br]$^+$409.

3-benzyloxy-5β-estr-15-en-17-one ethyleneketal (Compound 8)

Dried compound 7 (3 g, 6.1 mmol) by distillation of with dry solution (2×20 ml) was dissolved in dry benzene (40 ml) and dry DMSO (20 ml) and potassium t-butoxide (2.0 g) was slowly added. The mixture was stirred and heated to 60 C under nitrogen. After 20 h the product was cooled and brine (50 ml) was added. The mixture was extracted with benzene, washed with brine and the solvents removed under reduced pressure. The crude oily dark compound was dissolved hexane and mixed with silica gel (6 g) and poured onto a flash-chromatography column. Elution with diethyl ether:hexane (9:1) give 1.4 g (56.2% yield) the title compound as an oily compound. The crude oil was subjected to deprotection without additional purification.

TLC: Eluant: Diethyl ether:Hexane (1:1), $R_f$ 0.54. MS: m/z ($M^+$) 408.

3-Benzyloxy-5β-estr-15-en-17-one (Compound 9)

To a solution of compound 8 (1.4 g, 3.4 mmol) in acetone:water 10:3 (65 ml), pyridinium p-toluenesulfonate (0.2 g, 0.6 mmol) was added. The mixture was stirred overnight and the deprotection monitored by TLC. The acetone was removed under reduced pressure and the product extracted by hexane. The hexane solution was washed with brine, dried on $Na_2SO_4$ and the hexane removed under reduced pressure. When a mixture of 3a and 3b isomers was obtained, they were separated at this stage by chromatography. Flash-chromatography on silica gel with diethyl ether:hexane (1:1) as eluant give 1.0 g (80.0% yield) the title compound as a white solid, two isomers, which were crystallized from methanol:diethyl ether (1:1).

9a: TLC: Eluant: Diethyl ether:hexane (1:1), $R_f$=0.50. m.p. 92–94° C. MS: m/z (M$^+$)364, [M-15]$^+$ 273. IR 1707 cm$^{-1}$. $^1$H NMR: δ=7.52(d, 1H, H—C[16]), 7.34(m, 5H, Ph), 6.02(d×d, 1H, H—C[15]), 4.56(s, 2H CH$_2$Ph), 3.4 (m, 1H, H—C[3]) 1.06(s, 3H, CH$_3$[18]). C$_{25}$H$_{32}$O$_2$ (MW 864), Cal. C, 82.42%; H, 8.79%. Found: C, 82.10%; H. 8.80%. X ray diffraction measurements proved the above structural determination.

9b: TLC: Eluant: Diethyl ether:hexane (1:1), $R_f$=0.59. m.p. 119–120° C. MS: m/z (M$^+$)364, [M-15]$^+$ 273. IR 1707 cm$^{-1}$. $^1$H NMR: δ=7.52(d, 1H, H—C[16]), 7.32(m, 5H, Ph), 6.02(d×d, 1H, H—C[15]), 4.48(s, 2H CH$_2$Ph), 3.74 (m, 1H, H—C[3]) 1.08(s, 3H, CH$_3$[18']). C$_{25}$H$_{32}$O$_2$ (MW 864), Cal. C, 82.42%; H, 8.79%. Found: C, 82.13%; H, 8.80%.

4(3'-benzyloxy-17'β-hydroxy-5'β-estr-15'-en-17'α-yl)furan-2-carbaldehyde ethylene acetal (Compound 10)

To a solution of 4Br-2furaldehyde ethylene acetal (2.5 g, 11.4 mmol) in freshly distilled dry THF (10 ml) cooled to −70° C. under N$_2$, 2.5 M n-butyllithium (4.0 ml, 10 mmol) was slowly added. After 30 min at −70° C. compound 9 (2.0 g, 5.5 mmol) dissolved in dry THF (20 ml) was added through a syringe. After 1 h at −70° C. the mixture was allowed to warm up to −10° C. and citric acid (100 mM, 10 ml) was slowly added. The product was extracted with diethyl ether, washed 100 mM citric acid (30 ml) and water, and dried and the solvents removed under reduced pressure. The product was purifed by flash-chromatography on silica gel with diethyl ether:hexane (7:3) as eluant to give 2.3 g (82.9% yield) the title compound as a white solid.

10a: TLC, Eluant: Diethyl ether:Hexane (7:3), R$_f$ 0.40. MS: m/z (M$^+$) 504, [M-H$_2$O]$^+$486. IR 3550 cm$^{-1}$. $^1$H NMR: δ=7.33(m, 5H, Ph), 7.18(s, 1H, H—C[5], 6.42(s, 1H, H—C[3])6.06 (d, 1H, H—C[16']), 5.89(s, 1H, H—C—C[2]), 5.58(d×d, 1H, H—C[15']), 4.54(s, 2H CH$_2$Ph), 4.08(m,4H, OCH$_2$CH$_2$O), 3.36(m, 1H, H—C[3']) 1.02(s, 3H, CH$_3$[18']).

10b: Eluant: Diethyl ether:Hexane (7:3), $R_f$=0.50. MS: m/z (M$^+$)504, [M-H$_2$O]$^+$, 486. IR 3550 cm$^{-1}$. $^1$H NMR: δ=7.33(m, 5H, Ph), 7.18(s, 1H, H—C[5]), 6.46(s, 1H, H—C[3])6.07(d, 1H, H—C[16']), 5.87(s, 1H, H—C—C[2]), 5.70 (d×d, 1H, H—C[15']), 4.47(s, 2H CH$_2$Ph), 4.08(m,4H, OCH$_2$CH$_2$O), 3.71(m, 1H, H—C[3']) 1.04(s, 3H, CH$_3$[18']).

4-(3'-benzyloxy-17'β-Acetyl-5'β-estr-15'-en-17'α-yl)furan-2-carbaldehyde ethylene acetal (Compound 11)

Compound 10 (2.3 g, 4.5 mmol) was dissolved in a mixture of pyridine (20 ml), acetic anhydride (10 ml) and dimethylaminopyridine (100 mg) and stirred overnight at room temperature. The reaction was stopped by addition of 0.5 M HCl (30 ml) and the product extracted with diethyl ether, washed with 5% NaHCO$_3$, dried on Na$_2$SO$_4$ and the solvent evaporated under reduced pressure to give 2.4 g, (97.6% yield) the title compound as an oil.

11a: TLC: Eluant: Diethyl ether:hexane (7:3), $R_f$=0.6. MS: m/z [M-60]$^+$ 486. $^1$H NMR: δ=7.32(m, 5H, Ph), 7.19(s, 1H, H—C[5]), 6.39(d, 1H, H—C [15']), 6.28(s, 1H, H—C[3]) 6.10(d, 1H, H—C[16']) 5.87(s, 1H, H—C—C[2]), 5.68 (d×d, 1H, H—C[15']), 4.52(s, 2H CH$_2$Ph), 4.08(m,4H, OCH$_2$CH$_2$O), 3.36(m, 1H, H—C[3']), 2.02 (s,3H, OCOCH$_3$), 1.02(s, 3H, CH$_3$[18']).

11b: TLC: Eluant: Diethyl ether:hexane (7:3), $R_f$=0.7. MS: m/z [M-60]$^+$486.

4-(3'-benzyloxy-15'β-hydroxy-5'βestr-16'-en-17'-yl)furan-2-carbaldehyde ethylene acetal (Compound 12)

Compound 11 (1.8 g, 3.3mmol) was dissolved in acetone (75 ml) and water (15 ml) and CaCO$_3$ (1 g) was added. The mixture was stirred and boiled for 3 days and the reaction monitored by TLC. After filtration, the acetone was removed under reduced pressure and the product dissolved in ether, washed with water, dried on Na$_2$SO$_4$ and the solvent removed and the product was purified by flash-chromatography on silica gel with diethyl ether:hexane (7:3) as eluant give 0.9 g (54.1% yield) the title compound as a white solid.

12a: TLC: Eluant: diethyl ether:hexane (1:1). $R_f$=0.35. MS: m/z (M$^+$) 504, [M-H$_2$O]$^+$, 486. IR 3550 cm$^{-1}$. $^1$H NMR(CDCl$_3$) δ=7.52(s, 1H, H—C[5]), 7.32(m, 5H, Ph), 6.57(s, 1H, H—C[3]), 5.94(d, 1H, H—C[16']), 5.90(s, 1H, H—C—C[2]), 4.57(m, 1H, H—C[15'] and s, 2H, CH$_2$Ph), 4.08(m,4H, OCH$_2$CH$_2$O), 3.40(m, 1H, H—C[3']) 1.28(s, 3H, CH$_3$[18']).

12b: TLC: Eluant: Diethyl ether:hexane (1:1). $R_f$=0.4. MS: m/z (M$^+$) 504, [M-H$_2$O]$^+$, 486. IR 3550 cm$^{-1}$. $^1$H NMR: δ=7.52(s, 1H, H—C[5]), 7.34(m, 5H, Ph), 6.57(s, 1H, H—C[3]), 5.96(d, 1H, H—C[16']), 5.90(s, 1H, H—C—C [2]), 4.56(m, 1H, H—C[15']), 4.50(s, 2H, CH$_2$Ph), 4.08(m, 4H, OCH$_2$CH$_2$O), 3.74(m, 1H, H—C[3']) 1.28(s, 3H, CH$_3$[18']).

4-('3-benzyloxy-15'β-hydroxy-5β-estran-17'β-yl)furan-2-carbaldehyde ethylene acetal (Compound 13)

Compound 12 (0.5 g, 0.9 mmol) was dissolved in THF (9 ml), methanol (20 ml) and 5% NaOAc (0.6 ml), mixed with 10% Pd/CaCO$_3$ (150 mg) and subjected to hydrogenation at 50 psi for 6 hr. The solution was filtered and the solvent evaporated under reduced pressure, redissolved in dichloromethane, washed with water, dried on Na$_2$SO$_4$ and the solvent evaporated under reduced pressure to give 500 mg, (99% yield) the title compound as a white solid.

X-ray diffraction measurements of 4-(3'α-benzyloxy-15'β-hydroxy-5'β-estran-17'β-yl)furan-2-carbaldehyde ethylene acetal product showed the (17'β-yl) configuration.

13a: TLC: Eluant: Diethyl ether:hexane (7:3). $R_f$=0.34. MS: m/z (M$^+$) 506, [M-H$_2$O]$^+$, 488. IR 8550 cm$^{-1}$.$^1$H NMR: δ=7.34(m, 5H, Ph), 7.20(s, $^1$H, H—C[5]), 6.38(s, 1H, H—C[8]), 5.85(s, 1H, H—C—C[2]), 4.56(s, 2H, CH$_2$Ph), 4.35(t, 1H, H—C[15']), 4.08(m,4H, OCH$_2$CH$_2$O), 3.40(m, 1H, H—C[3']) 0.78(s, 3H, CH$_3$[18']).

13b: TLC: Eluant: diethyl ether:hexane (7:3). $R_f$=0.4. MS: m/z (M$^+$) 506, [M-H$_2$O]$^+$488. $^1$H NMR: δ=7.32(m, 5H, Ph), 7.21(s, 1H, H—C[5]), 6.38(s, 1H, H—C[3]), 5.84(s, 1H, H—C—C[2]), 4.48(d, 2H, CH$_2$Ph), 4.35(t, 1H, H—C[15']), 4.08(m,4H, OCH$_2$CH$_2$O), 3.72(m, 1H, H—C[3']) 0.96(s, 3H, CH$_3$ [18']).

4-('3-benzyloxy-15'β-hydroxy-5β-estran-17'β-yl)furan-2-carbaldehyde (Compound 13-1).

A solution of compound 13 (200 ml, 0.39 mmol) in THF (15 ml) and 1N HCl (3 ml) was stirred for 3 hr. The solution was cooled to room temperature, and extracted twice with ether. The ethereal solution was washed with 5% NaHCO$_3$, and water, and died over anhydrous Na$_2$SO$_4$ and the solvent removed at reduced pressure to give 120 mg (67% yield) as an oily product.

13a-1: TLC: Eluant: hexane:diethyl ether (2:8), R$_f$: 0.5. MS (EI): m/z (M$^+$) 462, [M-H$_2$O]$^+$444. 13b-1TLC: Eluant: hexane:diethyl ether (2:8), R$_f$: 0.5. MS (EI): m/z (M$^+$) 462; [M-H$_2$O]$^+$ 444.

4-(-('3-benzyloxy-15'β-hydroxy-5β-estran-17'β-yl)furan-2-methyl alcohol (Compound 13-2).

To a solution of compound 13-1 (100 mg, 0.20 mmol) in THF (15 ml) and methanol (3 ml), NaBH$_4$ (100 mg) was slowly added. After the exothermic reaction was completed the solution was stirred for 1 hr. Water (10 ml) was added and stirred for 15 min. The organic solvent were removed under low pressure and the remaining solution was extracted with diethyl ether washed with water and dried on Na$_2$SO$_4$. The organic solvent was removed under reduced pressure to give 100 mg (99% yield) as an oily product.

13a-2:TLC: Eluant: hexane:diethyl ether (2:8), R$_f$: 0.3. MS: m/z (M$^{+\cdot}$) 464, [M-H$_2$O]$^{+\cdot}$ 446. 13b-2: TLC: Eluant: hexane:diethyl ether (2:8), R$_f$: 0.3. MS: m/z (M$^{+\cdot}$) 464, [M-H$^2$O]$^{+\cdot}$ 446.

4-(3'β,15'βdihydroxy-5β-estran-17β-yl)furan-2-methyl alcohol (Compound 13-3).

A solution of compound 13-2 (120 mg) in toluene/ethanol 1:2 (15 ml) and cyclohexene (0.2 ml) and Pd (OH)$_2$/C (50 mg) was refluxed for 4 hr. The solution was filtered and the solvent removed at low pressure to give 70 mg (72% yield) the title product as a white powder.

13a-3: MS: m/z (M$^{+\cdot}$) 374, [M-H$_2$O]$^{+\cdot}$ 356. $^1$H NMR: δ=7.20(s, 1H, H—C[5]), 6.38*s, 1H, H—([3]) 4.50(s, 2H, CH$_2$—O), 4.35(m, 1H, H—C[15']), 3.40(m, 1H, H—([3']) 0.78(s, 3H, CH$_3$ [18']). 13b-3: 13a-3: MS: m/z (M$^{+\cdot}$) 374, [M-H$^2$O]$^{+\cdot}$ 356. $^1$H NMR: δ=7.20(s, 1H, H—C[5]), 6.16(s, 1H, H—C[3]), 4.50(s, 2H, CH$_2$—O), 4.35(m, 1H, H—C[15']), 3.59(m, 1H, H—C[3']) 0.78(s, 3H, CH$_3$[18']).

4-(3'-benzyloxy-5'β-estr-14'-en-17'β-yl)furan-2-carbaldehyde ethylene acetal (Compound 14).

Compound 13 (300 mg, 0.59 mmol) was dissolved in dry pyridine (3 ml), cooled on ice and treated with SOCl$_2$ (0.15 ml, 0.19 mmol). After 30 min the solution was diluted with diethyl ether, washed with 10% citric acid (10 ml) and 5% NaHCO$_3$ (10 ml), dried over anhydrous Na$_2$SO$_4$ and the solvent removed at reduced pressure. The crude product the product was purified by flash-chromatography on silica gel with acetone:hexane (1:4) as eluant to give 220 mg (73% yield) the title compound as a white solid.

14a: TLC: Eluant: Diethyl ether, R$_f$=0.8 MS: m/z (M$^{+\cdot}$) 488, [M-CH$_3$]$^+$473. 14b: TLC: Eluant: diethyl ether, R$_f$=0.9 MS: m/z (M$^{+\cdot}$) 488, [M-CH$_3$]$^+$473.

4-(3'-benzyloxy-5'β-estr-14 '-en-17'β-yl)-2,5-dihydroxy-3-pentenal ethylene acetal (Compound 16).

To a stirred solution of compound 14 (200 mg, 0.4 mmol) in dioxane/water 12:3 (10 ml), AcONa (40 mg, NBS (180 mg, 1 mmol) was slowly added. Then NaBH$_4$ (50 mg) was slowly added. After 2 hr the mixture was extracted with diethyl ether, dried over anhydrous Na$_2$SO$_4$ and the solvent removed at reduced presse to give 180 mg (88.5% yield) as an oil. The crude oily product was subjected to cyclization reaction without additional purification.

16a: IR: 3436 (OH). 16b: IR; 3430 (OH).

5-(3'-benzyloxy-5'β-estr-14'-en-17'β-yl)-3,6-dihydro-2H-pyran-2,3-diol (Compound 17).

A solution of compound 16 (200 mg, 0.39 mmol) in THF (9 ml) and 1N HCl (3 ml) was stirred and boiled for 5 hr. The solution was cooled to room temperature, and extracted twice with ether. The ethereal solution was washed with 5% NaHCO$_3$, and water, and dried over anhydrous Na$_2$SO$_4$ and the solvent removed at reduced pressure. The crude product was purified by flash-chromatography on silica gel with acetone: hexane (1:4) as eluant to give 150 mg (73% yield) the title compound as oil.

17a: TLC: Eluant: Hexane:Diethyl ether (3:7), R$_f$=0.35. 17b: TLC: Eluant: Hexane:Diethyl ether (3:7), R$_f$=0.32.

5-(3'-benzyloxy-5'β-estr-14'-en-17'β-yl)-2H-pyran-2-one (Compound 18).

A solution of compound 17 (500 mg) dissolved in CH$_2$Cl$_2$ (20 ml) and cooled in an ice bath was treated with PCC (250 mg) and stirred for one hour. The solution was filtered and the solvent removed by reduced pressure. The crude product was purified by flash-chromatography on silica gel with dichloromethane:methanol (95:5) as eluant to give 300 mg (62% yield) of the title compound as oil.

18a: IR: 1732(C=O), 1650(C=C). UV: 298 nm. $^1$H NMR (CDCl$_3$) δ=7.39(m, 5H, Ph), 7.34(s, H—C[6]),6.46(d, H—C[3]), 6.08(d, H—C[4]), 5.79d,H—C[15']), 4.47(d, CH$_2$Ph), 8.40(br, H—C[3']), 0.78(s, 3H, CH$_3$ [18']). 18b: IR: 1732(C=O), 1650(C=C). UV: 298 nm $^1$H NMR (CDCl$_3$) δ=7.39(m, 5H, Ph), 7.34(m, H—C[6]),6.46(d, H—C[3]), 6.08(s, H—C[4]), 5.79d,H—C[15']), 4.47(d, CH$_2$Ph), 3.70 (br, H—C[3']), 0.78(s, 3H, CH$_3$ [18']).

5-(3'hydroxy-5'β-estr-14'-en-17'β-yl)-2H-pyran-2-one (Compound 19).

A solution of compound 18 (120 mg) in ethanol/toluene 2:1 (20 ml), cyclohexene (0.1 ml) and Pd(OH)$_2$ (50 mg) was boiled for 4 hr. The solution was filtered and the solvent evaporated at low pressure to give 60 mg (62%) of the title compound as an oil.

19a: IR: 1732(C=O), 1650(C=C). UV: 298 nm. 19b: IR: 1732(C=O), 1650(C=C). UV: 298 nm.

5-(3'-hydroxy-5'β-estran-14'hydroxy-17'β-yl)-2H-pyran-2-one (Compound 20).

Compound 19 (30 mg) dissolved in 2 ml of acetone/H$_2$O 9:1 add two drops of 1% HClO$_4$ solutions was treated with NBS (15 mg) and left at RT for 30 min The mixture was diluted with CH$_2$Cl$_2$ and washed with saturated NaHSO$_3$ solution and H$_2$O, dried on Na$_2$SO$_4$ and evaporated to dryness. The residue was dissolved in 2 ml methanol/CH$_2$Cl$_2$ 1:1, and NaOAc (2 mg) and excess of Raney-Ni (10–20 mg) were added. After 20 min of stirring the Raney-Ni was filtered off and the solution evaporated to dryness. The residue was purified on flash-chromatography CHCl$_2$Cl$_2$/methanol 95:5 as eluant to give 4 mg (25% yield) of the title compound as an oil.

20a: IR: 1732(C=C), 1650(C=C). UV: 298 nm. 20b: IR: 1730(C=C), 1650(C=C). UV: 298 nm.

Pharmacological Activity

Example 1

Total and Na$^+$ and K$^+$ dependent ATPase activities were measured in rat brain microsomal fraction. Enzyme activity was measured by the colorimetric determination of inorganic phosphate after the incubation of microsomes (30 µg protein/reaction) at 37° C. in a solution (final volume 500 µl) containing (final concentrations) Tris-HCl (50 nM, pH 7.4), NaCl (100 mM), KCl (10 mM), MgCl$_2$ (4 mM) and ATP (2 mM, Tris, vanadium free). After 10 minutes preincubation, the ATP was added to initiate the reaction. Reactions were terminated by the addition of 100 µl 5% trichloroacetic acid and the precipitate was removed by centrifugation. Mg$^{++}$-ATPase activity was determined by the addition of ouabain (1 mM) to the assay mixture.

Compounds 13–20 are inhibitors of Na$^+$,K$^+$-ATPase activity. As shown in Table 1 the compounds inhibit dose-dependently the activity of the Na$^+$,K$^+$-ATPase without significantly affecting the activity of the Mg$^{++}$-ATPase.

TABLE 1

Effect of the synthetic compounds on Na+, K+-ATPase activity

| Compound 13b nM | Na+, K+-ATPase activity (% of control) | Mg++-ATPase activity (% of control) |
|---|---|---|
| 1 | 100 | 100 |
| 10 | 64 | 86 |
| 100 | 38 | 88 |

TABLE 1-continued

Effect of the synthetic compounds on Na+, K+-ATPase activity

| Compound 13b nM | Na+, K+-ATPase activity (% of control) | Mg++-ATPase activity (% of control) |
|---|---|---|
| 1000 | 22 | 89 |
| 10000 | 2 | 86 |

Example 2

1. Effect of the Synthetic Compounds on Heart Muscle Contractility

Experiments were conducted on frog atrial muscle or guinea pigs atrium. The animals were anaesthetized by MS22 (frogs) or pentobarbital (guinea pigs) (10 mg/kg). Their hearts were removed quickly into Krebs-Henseleit buffer. Atrial strips were mounted vertically in a chamber at 37° C. The muscle contractility was recorded by a transducer (FSG-01, Experimentia) connected to a computer Acodas software (DataQ instruments). Results are shown in FIGS. 3a and 3b.

FIG. 3a. The increase of heart muscle contractility is evident by the increase in force amplitude following 10 minutes after the addition of compound 13b to guinea pig muscle strip.

Figure 3B:
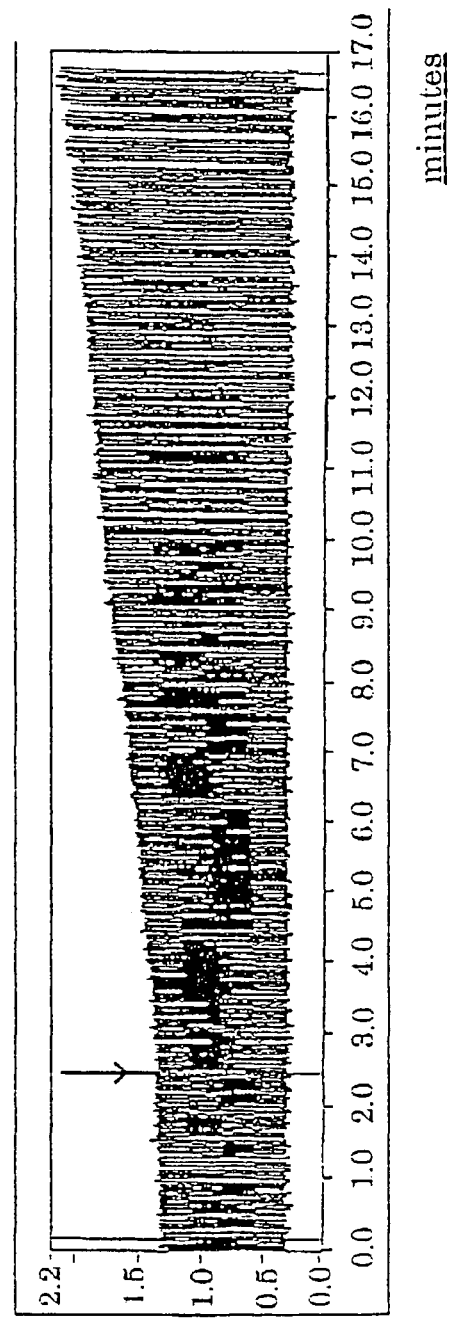

FIG. 3b. The effect of compound 17b at 10 nM to frog atrial muscle.

Figure 5A:
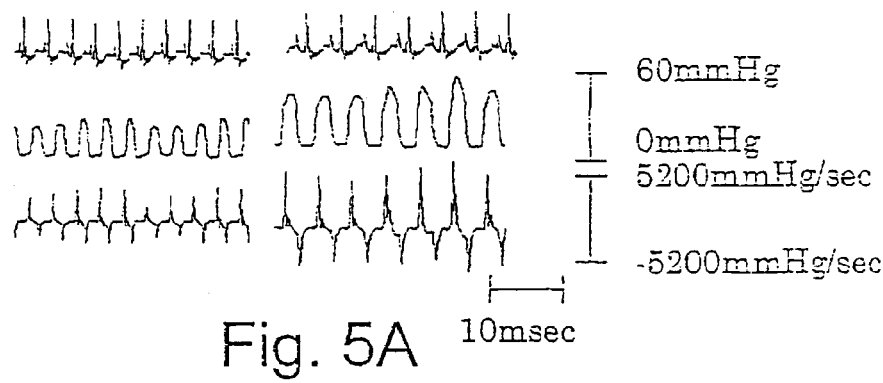
FIGS. 5a to 5d Effect of compounds of the invention and of digoxin on guinea pig atrial muscle contractility.

2. Monitoring the Effect of the Synthetic Compounds of the Invention and of Digoxin on Heart Muscle Contractility in vivo 2.6 mg/kg of compound 13-3 (β isomer) were injected to guinea pigs. Intraventricular pressure was monitored using a Millar catheter. Compound 13-3 induced an elevation in cardiac contractility, as evident from all cardiac parameters (FIG. 5A and Table 2). The traces on the left are control recordings and those on the right are recordings obtained 30 min post-inject on. The upper traces depict ECG recording from a subcutaneous electrode (lead II). The middle traces show left ventricle pressure and the lower traces the dp/dt (change in pressure with time).

Figure 5B:
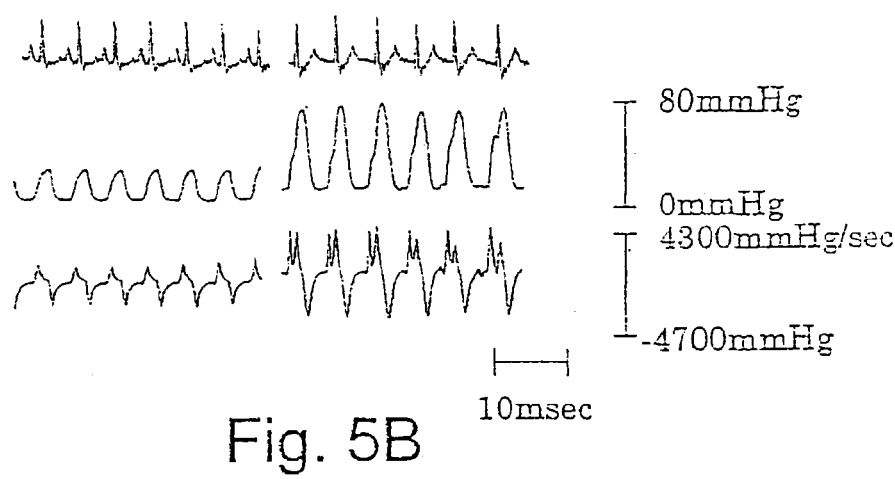

The injection of digoxin (2 mg/kg) caused increase in contractilty, as evident from the increase in the left ventricle systolic pressure and dp/dt (Table 2). Digoxin also induced bradycardia at this dose (FIG. 5B).

Figures 5C, 5D:
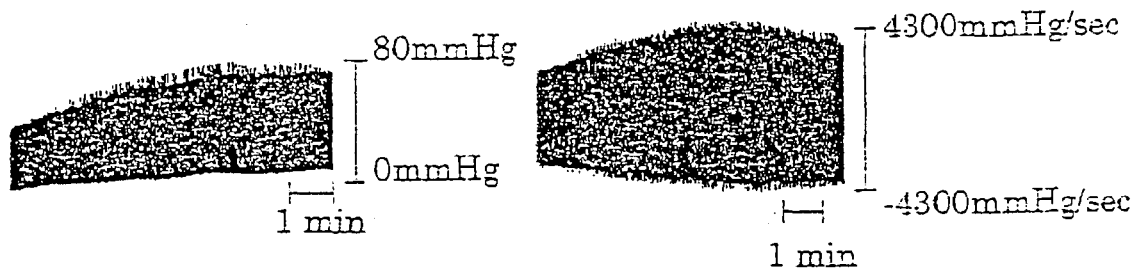

FIG. 5c also shows the effect of compound 13-3 on left ventricle pressure and dp/dt at a different time scale (10 min).

TABLE 2

Effects of compound 13-3 and digoxin on cardiac contractility in vivo

| | Control | 13-3 (10 min after injection) | 13-3 (33 min post injection) | 13-3 (7 hr. post injection) | Control | Digoxin | Death after 40 min |
|---|---|---|---|---|---|---|---|
| HR (beat/min) | 226.2 | 295.74 | 325 | 340 | 327 | 300 | |
| LVEDP (mmHg) | 5.52 | 51.70 | 51.98 | 37.57 | 17.3 | 49.78 | |
| LVSP (mmHg) | 10.83 | 67.88 | 124.61 | 107.45 | 75 | 232.4 | |
| dp/dt (mmHg/sec) | 2248.19 | 3319.11 | 4215.86 | 5146.12 | 1620.7 | 4248.4 | |

HR - heart rate; LVEDP - left ventricle end diastolic pressure;
LVSP-left ventricle systolic pressure; dp/dt - change in pressure with time.
13-3 - the β isomer of compound 13-3.

Example 3

Digoxin-Antagonizing Effect

Guinea pigs were maintained under anesthesia, the jugular artery was catheterized and blood pressure was monitored via a pressure transducer. Two ECG electrodes were placed under the skin and ECG was monitored following amplification.

2.5 mg/kg of compound 13-3 or digoxin were subcutaneously injected to the guinea pigs.

Figure 6A:
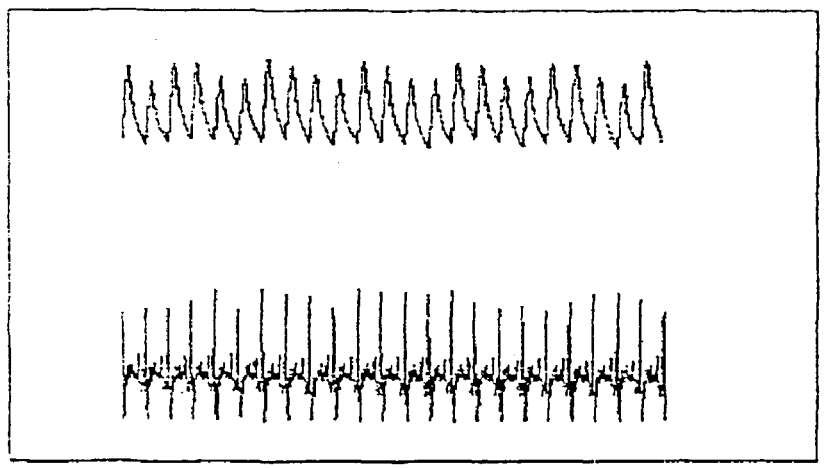
FIGS. 6a to 6c EGG and changes in blood pressure in guinea pigs treated with compound 13-3 (α isomer) and with digoxin.
Figure 6B:
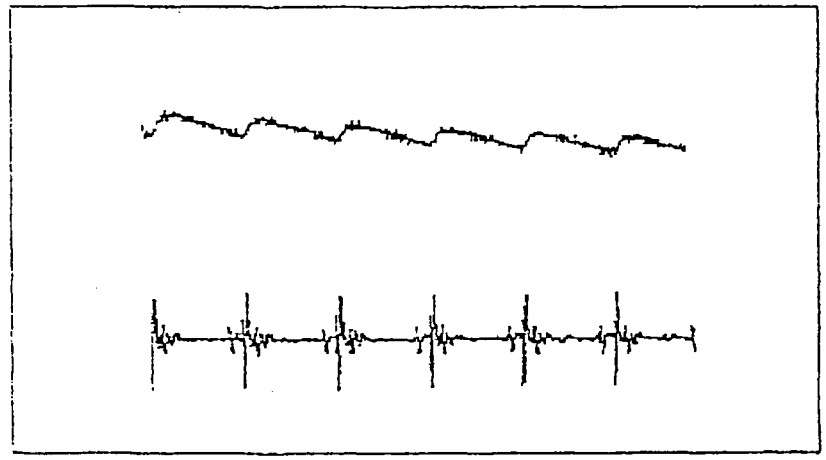
Figure 6C:
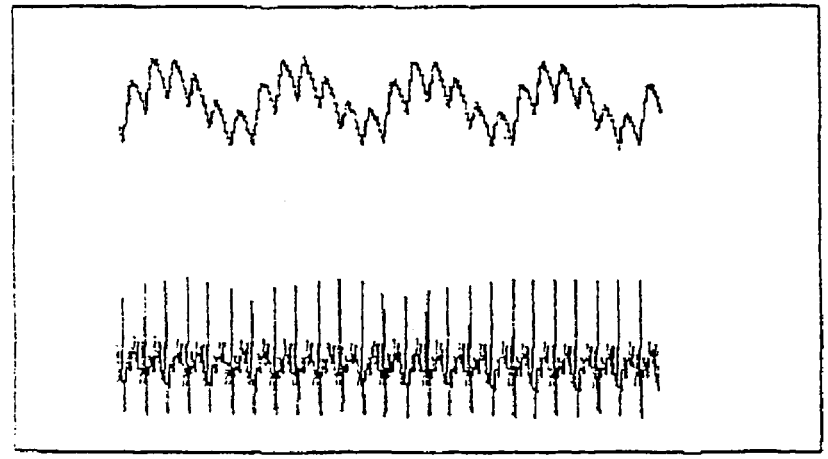

FIGS. 6a to 6c snow changes in blood pressure recorded from the jugular artery (upper traces) and EGG recorded by the two subcutaneous electrodes (lower traces).

Injection of 2.5 mg/kg of compound 13-3 (α isomer, dissolved in ethanol/polyethylene glycol solution, subcutaneously) is shown in FIG. 6A. Injection of digoxin (2.5 mg/kg, subcutaneously) induced lethal cardiac arrhythmia after 2.5 hours (FIG. 6B). Injection of 2.5 mg/kg of compound 13-3 (subcutaneously) 30 minutes before injection of 2.5 mg/kg digoxin prevented induction of cardiac arrhythmia (FIG. 6C).

The results in FIG. 6C show that compound antagonized the digoxin toxicity. It is to be noted that compound 13-3 was not toxic when injected to guinea pigs at doses of up to 13 mg/kg, and are thus not toxic.

Example 4

Effect of the Synthetic Compounds on Cell Differentiation
Morphological changes of K562 cells, grown in appropriate media, was followed. Results are shown in FIGS. 4a to 4f.

Figure 4A:
FIGS. 4a to 4f Effect of compounds of the invention on K562 cell differentiation.
Figure 4F:
Figure 4B:

FIG. 4a. Control cells after 2 days in culture.
FIG. 4b. Cells after 2 days in culture, the presence of $10^{-8}$M ouabain. Ouabain does not show any effects at this concentration.
FIG. 4c. Cells after 2 days in culture, in the presence of $10^{-8}$M compound 13b. The differentiation manifested in cells elongation should be noted.
FIG. 4d. Control cells after 6 days in culture.

Figure 4E:
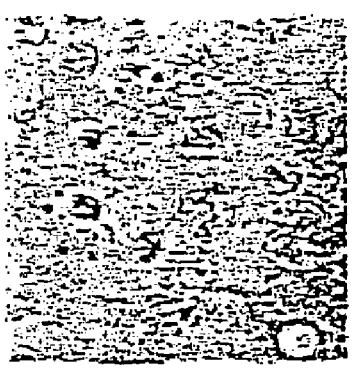
Figure 4C:
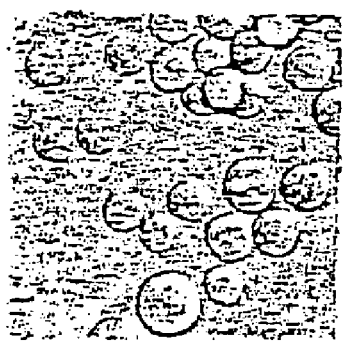
Figure 4D:
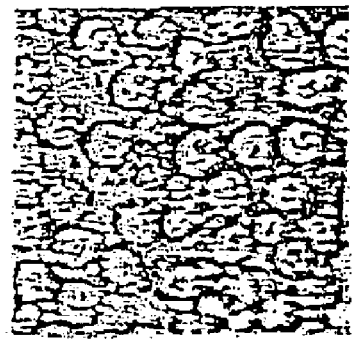

FIG. 4e. Cells after 6 days in culture, in the presence of 10⁻⁷M ouabain. Cell degradation and death is evident.

FIG. 4f. Cells after 6 days in culture, in the presence of 10⁻⁶M compound 13b. Cell elongation, indicative of differentiation, should be noted.

The invention claimed is:

1. A compound of formula (I)

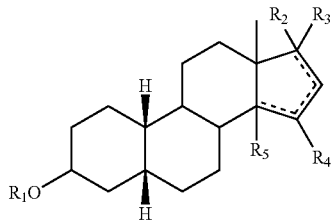

(I)

wherein
R$_1$ is hydrogen or a hydroxy protecting group;
R$_2$ is OH or hydrogen;
R$_3$ is selected from one of the following groups:

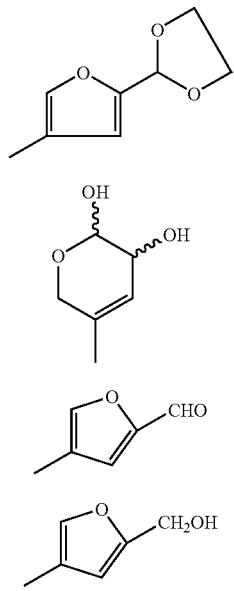

R$_4$ is hydrogen or OH;
R$_5$ is hydrogen or OH;
and the dashed line in formula (I) denotes an optional double bond; and isomers and pharmaceutically acceptable salts thereof.

2. A compound according to claim 1 wherein said hydroxy protecing group is selected from the group consisting of benzyl, amino acid, peptide and mono- and di-saccharide.

3. A compound according to claim 1 wherein R$_1$ is Bz, R$_2$ is OH, R$_3$ is the group (a) and R$_4$ and R$_5$ are hydrogen, having a double bond between the carbons at the 15 and 16 positions.

4. A compound according to claim 1 wherein R$_1$ is Bz, R$_2$ is a group (a), (b), (c) or (d), R$_4$ is OH and R$_5$ is hydrogen.

5. A compound according to claim 1 wherein R$_1$ is Bz, R$_2$ is hydrogen, R$_3$ is the group (a) and R$_4$ is hydrogen, having a double bond between the carbon atoms at the 14 and 15 positions.

6. A compound according to claim 1 wherein R$_1$ is Bz, R$_2$ is hydrogen, R$_3$ is the group (b) and R$_4$ is hydrogen, having a double bond between the carbon atoms at the 14 and 15 positions.

7. A compound according to claim 1 wherein R$_1$ is Bz, R$_2$ is hydrogen, R$_3$ is the group (c) and R$_4$ is hydrogen, having double bonds between the carbon atoms at the 14 and 15 positions.

8. A compound according to claim 1 wherein R$_1$ is hydrogen, R$_2$ is hydrogen, R$_3$ is the group (c), R$_4$ is hydrogen and R$_5$ is OH.

9. A process for the preparation of a compound of claim 1, wherein R$_3$ can additionally represent the group

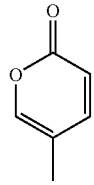

(e)

comprising the following steps:
a) hydrogenating the double bond of 19-nortestosterone to obtain 17β-hydroxy-5β-estran-3-one (designated compound 2);
b) oxidating the hydroxyl group of said compound 2 to obtain 5β-estrane-3,17-dione (designated compound 3);
c) reducing the carbonyl group at position 3 of said compound 3 to a hydroxyl group to obtain 3-hydroxy-5β-estran-17-one (designated compound 4);
d) reacting said compound 4 with ethylene glycol to obtain the ketal derivative thereof, 3-hydroxy-5β-estran-17-one ethylene ketal (designated compound 5);
e) reacting the hydroxyl group of said compound 5 with a hydroxyl protecting group to obtain 3-benezyloxy-5β-estran-17-one-ethylene ketal (designated compound 6);
f) brominating said compound 6 at position 16 to give 3-benzyloxy-16-bromo-5β-estran-17-one ethyelene ketal (designated compound 7) and subsequently dehydrobrominating said product, to obtain 3-benzyloxy-5β-estr-15-en-17-one ethylene ketal (designated compound 8);
g) removing the ketal group from said compound 8 to obtain 3-benzyloxy-5β-estr-15-en-17-one (designated compound 9);
h) reacting said compound 9 with 4-bromo-furfural ethylene acetal to obtain 4-(3'-benzyloxy-17'β-hydroxy-5'β-estr-15'-en-17'α-yl) furan-2-carbaldehyde ethylene acetal (designated compound 10);
i) reacting said compound 10 with acetic anhydride to obtain 4-(3'-benzyloxy-17'β-acetyl-5'β-estr-15'-en-17'α-yl) furan-2-carbaldehyde ethylene acetal (designated compound 11) and boiling the same with calcium carbonate to obtain 4-(3'-benzyloxy-15'β-hydroxy-5'β-estr-16'-en-17'-yl) furan-2-carbaldehyde ethylene acetal (designated compound 12) with the allylic hydroxyl in position 15, and a double bond between 16 and 17;

j) hydrogenating the double bond between the carbon atoms at the 16 and 17 positions of said compound 12, to yield 4-(3'-benzyloxy-15'β-hydroxy-5β-estran-17'β-yl) furan-2-carbaldehyde ethylene acetal (designated compound 13);

k) optionally hydrolyzing said compound 13 to give 4-(3'-benzyloxy-15'β-hydroxy-5'β-estrane-17'β-yl) furan-2-carbaldehyde ethylene acetal (designated compound 13-1) which may be reduced to give 4-(3'-benzyloxy-15'β-hydroxy-5β-estran-17'β-yl) furan-2-methyl alcohol (designated compound 13-2) which may be hydrogenolyzed to remove the hydroxy protecting group to give 4-(3'β,15'β-dihydroxy-5β-estran-17β-yl) furan-2-methyl alcohol (designated compound 13-3);

l) eliminating the hydroxyl group from compound 13, to give 4-(3'-benzyloxy-5'β-estr-14'-en-17'β-yl) furan-2-carbaldehyde ethylene acetal (designated compound 14);

m) Oxidating said compound 14 with NBS, and reducing the intermediate with $NaBH_4$ to give 4-(3-benzyloxy-5'β-estr-14'-en-17'β-yl)-2,5-dihydroxy-3-pentenal ethylene acetal (designated compound 16), followed by hydrolysis of the ethylene acetal and cyclization to give 5-(3'-benzyloxy-5'β-estr-14'-en-17'β-yl)-3,6-dihydro-2H-pyran-2,3,-diol (designated compound 17)

n) oxidating the hydroxyl group at the 2 position of the pyran functional group of said compound 17 followed by dehydratation of the additional hydroxyl group of said compound 17, to give 5-(3'-benzyloxy-5'β-estr-14'-en-17'β-yl)-2H-pyran-2-one (designated compound 18);

o) hydrogenolysing said compound 18 to remove the hydroxy protecting group from position 3 of said compound 18, to give 5-(3'-hydroxy-5β'-estr-14 '-en-17'β-yl)-3,6-dihydro-2H-pyran-2-one (designated compound 19); and p) hydroxylating said compound 19 at the 14 position by an addition reaction to obtain norbufalin (designated compound 20).

10. A pharmaceutical composition comprising as active ingredient the compound of claim 1 in a pharmaceutically acceptable carrier, optionally further comprising a pharmaceutically acceptable adjuvant, excipient or diluent.

11. A method of treating digoxin intoxicationin a patient, comprising the step of administering to said patient a therapeutically effective amount of the compound of claim 1.

12. A method of preparing a pharmaceutical composition comprising the step of admixing the compound of claim 1, with at least one conventional non-toxic, pharmaceutically acceptable carrier, diluent, aduvant and/or vehicle.

* * * * *

UNITED STATES PATENT AND TRADEMARK OFFICE
CERTIFICATE OF CORRECTION

PATENT NO. : 7,087,590 B2
APPLICATION NO. : 10/257884
DATED : August 8, 2006
INVENTOR(S) : David Lichtstein and Joseph Deutsch It is certified that error appears in the above-identified patent and that said Letters Patent is hereby corrected as shown below:

Cover page
Column 1, line 60, "30-ß-isomers" should read --3-ß-isomers--.
Column 2, line 20, "anid" should read --and--.
Column 3, line 11, "he" should read --line--.
Column 6, line 34, "Pd(O)$_2$" should read --Pd(OH)$_2$--.
Column 6, line 62, "Sα" should read --3α--.
Column 8, line 33, "call" should read --can--.
Column 8, line 63, "and so" should read --and to--.
Column 12, line 53, before "give" insert --to--.
Column 17, line 67, "inject on" should read --injection--.
Column 18, line 37, "snow changes" should read --show changes--.
Column 18, line 65, "$10^{-8}$M compound" should read --$10^{-9}$M compound--.
Column 22, line 20, "intoxicationin" should read --intoxication in--.

Signed and Sealed this

Fourteenth Day of November, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,087,590 B2 |
| APPLICATION NO. | : 10/257884 |
| DATED | : August 8, 2006 |
| INVENTOR(S) | : David Lichtstein and Joseph Deutsch |

It is certified that error appears in the above-identified patent and that said Letters Patent is hereby corrected as shown below:

On the title page after (22) PCT Filed: delete "Apr. 17, 2002" and insert --Apr. 16, 2001--.

Signed and Sealed this

Twenty-sixth Day of February, 2008

JON W. DUDAS
*Director of the United States Patent and Trademark Office*